(12) United States Patent
Kroll et al.

(10) Patent No.: US 7,043,301 B1
(45) Date of Patent: May 9, 2006

(54) IMPLANTABLE CARDIAC STIMULATION SYSTEM PROVIDING HIGH OUTPUT FAR-FIELD PACING AND METHOD

(75) Inventors: Mark W. Kroll, Simi Valley, CA (US); Eric Falkenberg, Simi Valley, CA (US)

(73) Assignee: Pacesetter, Inc., Sylmar, CA (US)

(*) Notice: Subject to any disclaimer, the term of this patent is extended or adjusted under 35 U.S.C. 154(b) by 592 days.

(21) Appl. No.: 10/269,397

(22) Filed: Oct. 11, 2002

(51) Int. Cl.
*A61N 1/368* (2006.01)
*A61N 1/36* (2006.01)

(52) U.S. Cl. .................... 607/9; 607/4; 607/17; 607/25

(58) Field of Classification Search .............. 607/4, 607/5, 9, 17, 25
See application file for complete search history.

(56) References Cited

U.S. PATENT DOCUMENTS

| | | | |
|---|---|---|---|
| 5,193,536 A * | 3/1993 | Mehra | 607/4 |
| 5,275,621 A * | 1/1994 | Mehra | 607/5 |
| 5,735,876 A | 4/1998 | Kroll et al. | 607/5 |
| 5,738,105 A * | 4/1998 | Kroll | 600/510 |
| 5,782,883 A | 7/1998 | Kroll et al. | 607/14 |
| 5,871,510 A | 2/1999 | Kroll et al. | 607/14 |
| 5,978,703 A | 11/1999 | Kroll et al. | 607/5 |
| 6,167,306 A | 12/2000 | Kroll et al. | 607/5 |
| 6,185,457 B1 | 2/2001 | Kroll et al. | 607/5 |
| 6,223,082 B1 | 4/2001 | Bakels et al. | 607/17 |
| 6,230,056 B1 | 5/2001 | Kroll | 607/9 |
| 6,314,319 B1 | 11/2001 | Kroll et al. | 607/5 |
| 6,751,504 B1 * | 6/2004 | Fishler | 607/25 |
| 6,754,528 B1 * | 6/2004 | Bardy et al. | 607/5 |
| 6,829,506 B1 | 12/2004 | Pastore et al. | 607/9 |
| 2002/0133198 A1 * | 9/2002 | Kramer et al. | 607/9 |

FOREIGN PATENT DOCUMENTS

| | | |
|---|---|---|
| WO | WO 93/19809 * | 10/1993 |
| WO | WO 00/13741 A1 | 3/2000 |
| WO | WO 00/57955 A1 | 10/2000 |
| WO | WO 01/36040 A1 | 5/2001 |

OTHER PUBLICATIONS

US 5,584,866, 12/1996, Kroll et al. (withdrawn)

* cited by examiner

*Primary Examiner*—Carl Layno

(57) ABSTRACT

An implantable cardiac stimulation device provides therapy for hearts having severe conduction abnormalities such as hearts suffering from congestive heart failure. The implantable cardiac stimulation device includes a pulse generator that provides pacing pulses having energies greater than about 0.1 millijoules and a lead system including a far-field electrode configuration that applies the pacing pulses to the heart. The lead system may further provide a near-field pacing electrode configuration and the device switches between the near-field pacing electrode configuration and the far-field pacing electrode configuration responsive to the measurement of a hemodynamic parameter such as QRS width.

32 Claims, 3 Drawing Sheets

IMPLANTABLE CARDIAC STIMULATION SYSTEM PROVIDING HIGH OUTPUT FAR-FIELD PACING AND METHOD

FIELD OF THE INVENTION

The present invention generally relates to an implantable cardiac stimulation system that provides electrical therapy to a patient's heart. The present invention more particularly relates to such a system that provides high output far-field pacing stimulation of the heart for treating, for example, congestive heart failure.

BACKGROUND OF THE INVENTION

Implantable cardiac devices are well known in the art. They may take the form of implantable defibrillators or cardioverters which treat accelerated rhythms of the heart such as fibrillation or implantable pacemakers which maintain the heart rate above a prescribed limit, such as, for example, to treat a bradycardia. Implantable cardiac devices are also known which incorporate both a pacemaker and a defibrillator.

A pacemaker may be considered as a pacing system. The pacing system is comprised of two major components. One component is a pulse generator which generates the pacing stimulation pulses and includes the electronic circuitry and the power cell or battery. The other component is the lead, or leads, having electrodes which electrically couple the pacemaker to the heart. A lead may provide both unipolar and bipolar pacing polarity electrode configurations. In unipolar pacing, the pacing stimulation pulses are applied between a single electrode carried by the lead, in electrical contact with the desired heart chamber, and the pulse generator case. The electrode serves as the cathode (negative pole) and the case serves as the anode (positive pole). In bipolar pacing, the pacing stimulation pulses are applied between a pair of closely spaced electrodes carried by the lead, in electrical contact with the desired heart chamber, one electrode serving as the anode and the other electrode serving as the cathode.

Pacemakers deliver pacing pulses to the heart to cause the stimulated heart chamber to contract when the patient's own intrinsic rhythm fails. To this end, pacemakers include sensing circuits that sense cardiac activity for the detection of intrinsic cardiac events such as intrinsic atrial events (P waves) and intrinsic ventricular events (R waves). By monitoring such P waves and/or R waves, the pacemaker circuits are able to determine the intrinsic rhythm of the heart and provide stimulation pacing pulses that force atrial and/or ventricular depolarizations at appropriate times in the cardiac cycle when required to help stabilize the electrical rhythm of the heart.

Pacemakers are described as single-chamber or dual-chamber systems. A single-chamber system stimulates and senses in one chamber of the heart (atrium or ventricle). A dual-chamber system stimulates and/or senses in both chambers of the heart (atrium and ventricle). Dual-chamber systems may typically be programmed to operate in either a dual-chamber mode or a single-chamber mode.

Traditionally, therapy delivery had been limited to the venous, or right side of the heart. The reason for this is that implanted electrodes can cause blood clot formation in some patients. If a blood clot were released arterially from the left heart, as for example the left ventricle, it could pass directly to the brain potentially resulting in a paralyzing or fatal stroke. However, a blood clot released from the right heart, as from the right ventricle, would pass into the lungs where the filtering action of the lungs would prevent a fatal or debilitating embolism in the brain.

Recently, new lead structures and methods have been proposed and even practiced for delivering cardiac rhythm management therapy to the left heart. These lead structures and methods avoid direct electrode placement within the left atrium and left ventricle of the heart by lead implantation within the coronary sinus region of the heart. As used herein, the phrase "coronary sinus region" refers to the vasculature of the left ventricle, including any portions of the coronary sinus, great cardiac vein, left marginal vein, left posterior ventricular vein, middle cardiac vein, and/or small cardiac vein or any other cardiac vein accessible by the coronary sinus.

It has been demonstrated that electrodes placed in the coronary sinus region of the heart may be used for left atrial pacing, left ventricular pacing, or cardioversion and defibrillation. These advancements enable implantable cardiac stimulation devices to address the needs of a patient population with left ventricular dysfunction and/or congestive heart failure which would benefit from left heart side pacing, either alone or in conjunction with right heart side pacing (bi-chamber pacing), and/or defibrillation.

Congestive heart failure (CHF) is a debilitating, end-stage disease in which abnormal function of the heart leads to inadequate blood flow to fulfill the needs of the body's tissues. Typically, the heart loses propulsive power because the cardiac muscle loses capacity to stretch and contract. Often, the ventricles do not adequately fill with blood between heartbeats and the valves regulating blood flow may become leaky, allowing regurgitation or backflow of blood. The impairment of arterial circulation deprives vital organs of oxygen and nutrients. Fatigue, weakness, and inability to carry out daily tasks may result.

Not all CHF patients suffer debilitating symptoms immediately. Some may live actively for years. Yet, with few exceptions, the disease is relentlessly progressive.

As CHF progresses, it tends to become increasingly difficult to manage. Even the compensatory responses it triggers in the body may themselves eventually complicate the clinical prognosis. For example, when the heart attempts to compensate for reduced cardiac output, it adds muscle causing the ventricles to grow in volume in an affempt to pump more blood with each heartbeat. This places a still higher demand on the heart's oxygen supply. If the oxygen supply falls short of the growing demand, as it often does, further injury to the heart may result. The additional muscle mass may also stiffen the heart walls to hamper rather than assist in providing cardiac output.

Current standard treatment for heart failure is typically centered around medical treatment using ACE inhibitors, diuretics, and digitalis. It has also been demonstrated that aerobic exercise may improve exercise tolerance, improve quality of life, and decrease symptoms. Only an option in 1 out of 200 cases, heart transplantation is also available. Other cardiac surgery is also indicated for only a small percentage of patients with particular etiologies. Although advances in pharmacological therapy have significantly improved the survival rate and quality of life of patients, patients who are refractory to drug therapy, have a poor prognosis and limited exercise tolerance. Cardiac pacing has been proposed as a new primary treatment for patients with drug-refractory CHF.

In patients with heart failure, the heart has often remodeled due to the disease, such that there is increased fibrosis between myocardial cells, a lengthening of the cells, varying degrees of hypertrophy and dilation, and up- and down-regulation of various receptors that affect ionic balance, AP conduction, and contraction. These variations in the CHF substrates often result in conduction abnormalities that may further worsen the heart's contraction synchrony.

Biventricular pacing has been proposed as a therapy for patients with congestive heart failure. It has been found that pacing both ventricles nearly simultaneously improves the contraction and synchronization of the left ventricle to improve performance of the heart. Unfortunately, a CHF patient with severe infarcts and conduction abnormalities will still not regain normal electrical activation sequence. The present invention provides a further form of pacing the heart of patients with CHF. The improved pacing restores normal activation sequencing for those CHF patients who have severe infarcts and conduction abnormalities.

SUMMARY

The present invention provides an implantable cardiac stimulation device comprising a pulse generator that provides pacing pulses having energies greater than about 0.1 millijoules and a lead system including a far-field electrode configuration that applies the pacing pulses to the heart. The pacing pulse energies are well above normal pacing pulse energies which together with the far-field pacing, will cause a reduction in the total depolarization time across the ventricles to restore synchrony.

The far-field electrode configuration may include a right ventricular electrode and a left ventricular electrode. The electrodes are preferably large area electrodes, such as defibrillation electrodes. The electrodes may be coil electrodes.

The device may further include a hemodynamic measuring circuit that measures a hemodynamic parameter of the heart. The pulse generator may then vary the pacing energies to effect the hemodynamic parameter. The hemodynamic parameter may be QRS width. The pulse generator may vary the pacing energies responsive to the measured hemodynamic parameter.

The lead system may further include a near-field pacing electrode configuration and a switch that selectively couples the pulse generator to the far-field and near-field electrode configurations. The switch preferably selectively couples the pulse generator to the far-field and near-field electrode configurations responsive to the measured hemodynamic parameter.

The present invention further provides an implantable cardiac stimulation device comprising stimulation means for providing pacing pulses having energies greater than about 0.1 millijoules, and lead means including a far-field electrode configuration for applying the pacing pulses to the heart.

The present invention still further provides a method of pacing a heart. The method includes the steps of providing pacing pulses having energies greater than about 0.1 millijoules, and applying the pacing pulses to the heart with a far-field electrode configuration.

The present invention still further provides a method of treating congestive heart failure of a heart with an implantable cardiac stimulation device. The method includes the steps of providing pacing pulses with the implantable cardiac stimulation device and applying the pacing pulses to the heart with an implanted far-field electrode configuration. The pacing pulses have energies of at least about 0.1 millijoules. The method may further include the steps of measuring a hemodynamic parameter of the heart and varying the pacing pulse energies responsive to the measured hemodynamic parameter. The hemodynamic parameter may be QRS width and the applying step may be commenced when the QRS width is greater than a first predetermined duration. The method may further include the step of applying pacing pulses to the heart with a near-field electrode configuration when the QRS width is below a second predetermined duration.

BRIEF DESCRIPTION OF THE DRAWINGS

Further features and advantages of the present invention may be more readily understood by reference to the following description taken in conjunction with the accompanying drawings, in which.

DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
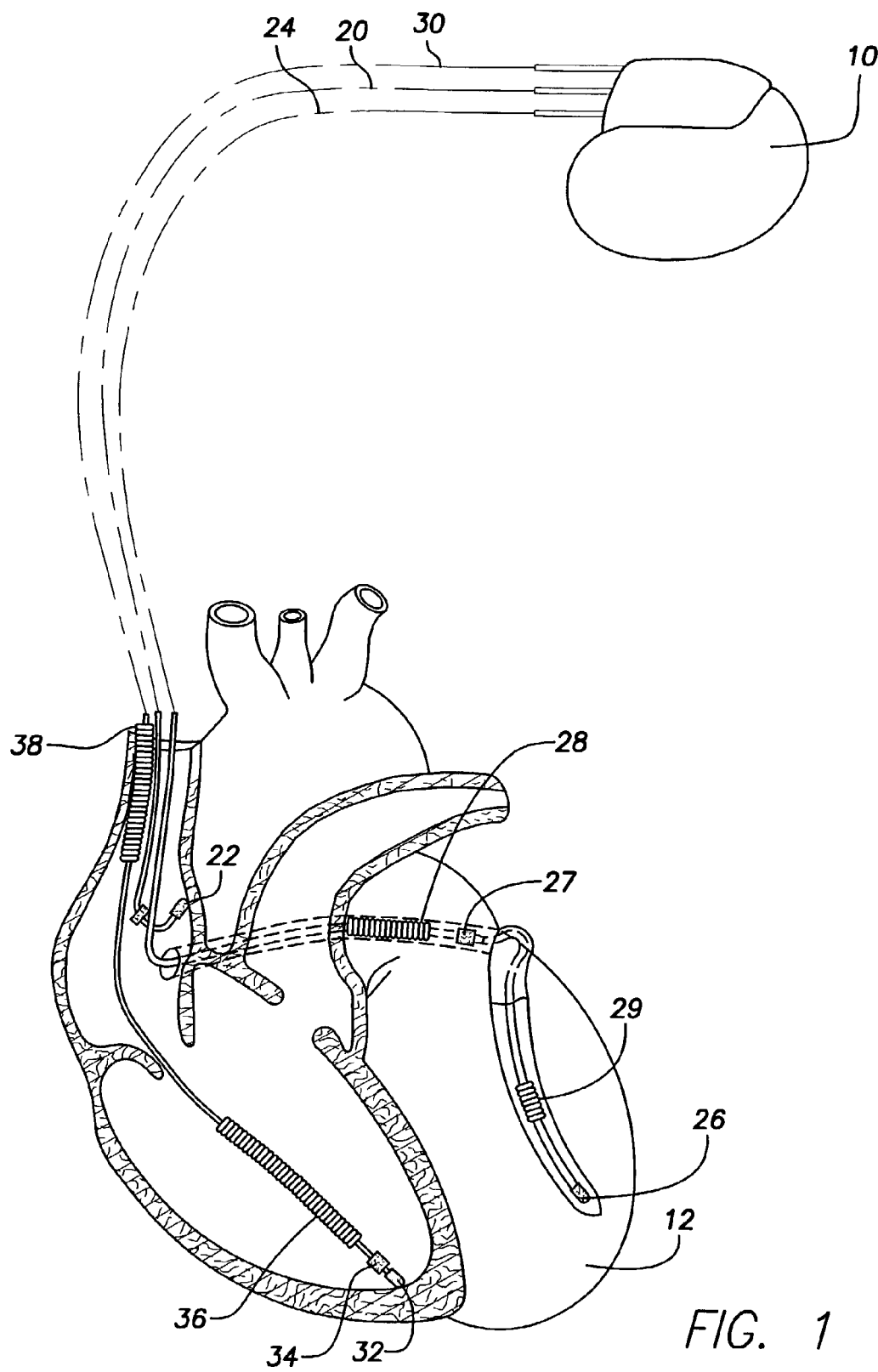
FIG. 1 is a simplified diagram illustrating an implantable stimulation device embodying the present invention in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial defibrillation coil electrode 28 or a left ventricular defibrillation coil electrode 29. As will be seen subsequently, the left ventricular coil electrode 29 may be used to advantage for high output far-field pacing of the heart in accordance with this embodiment of the present invention.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) defibrillation coil electrode 36, and an SVC defibrillation coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle. As will be also seen hereinafter, the right ventricular coil electrode 36 may be used to advantage for high output far-field pacing of the heart in accordance with this embodiment of the present invention in addition to providing defibrillation therapy.

Figure 2:
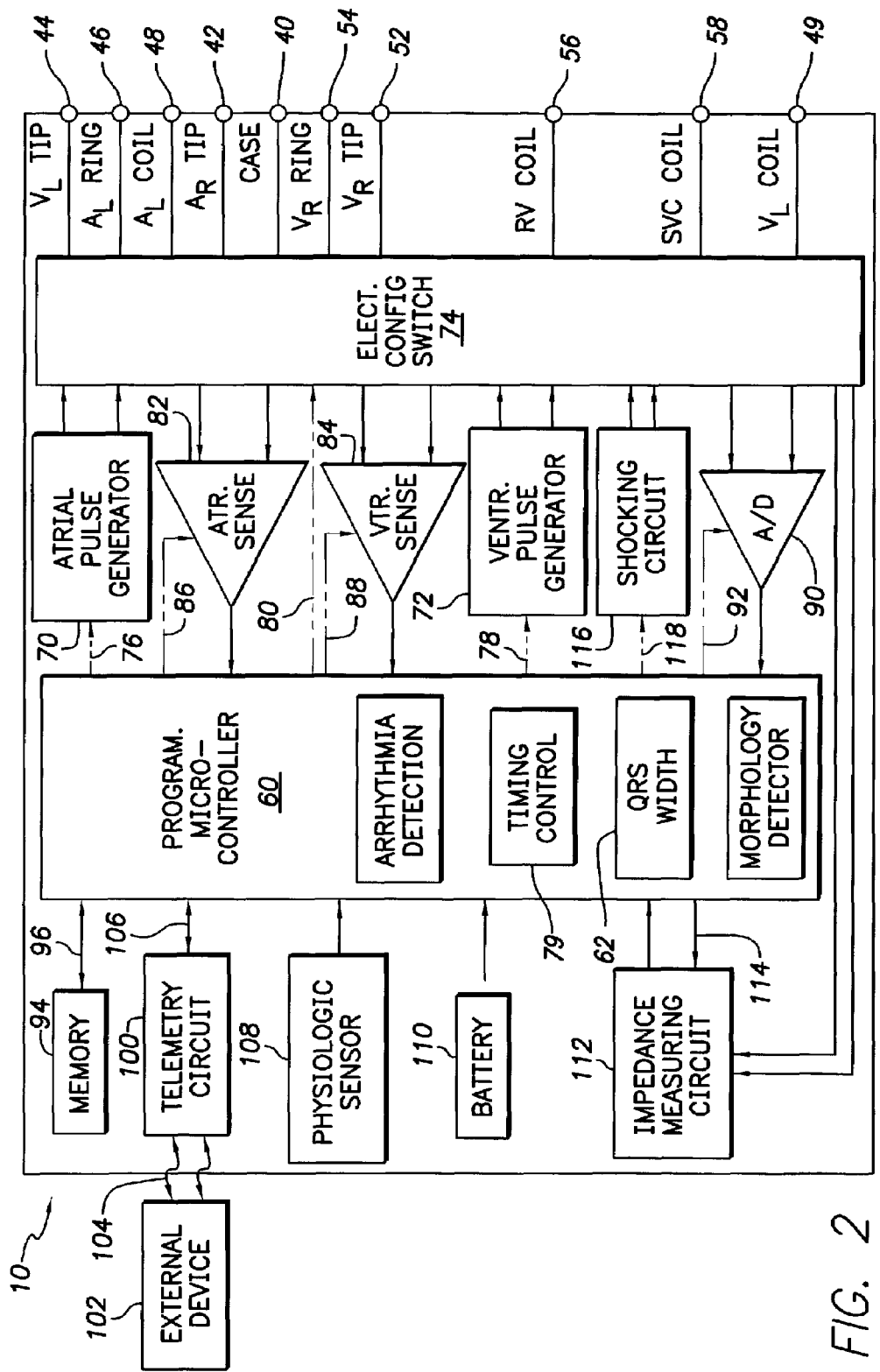
FIG. 2 is a functional block diagram of the implantable stimulation device of FIG. 1 illustrating the basic elements thereof for providing cardioversion, defibrillation and pacing stimulation in four chambers of the heart and high output far-field pacing in accordance with the present invention.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation and high output far-field pacing in accordance with the present invention. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 49, 52, 54, 56, and 58 (shown schematically and, for convenience, the names of the electrodes to which they are connected are shown next to the terminals). As such, to achieve right atrial sensing and pacing, the connector includes at least a right atrial tip terminal (AR TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, a left atrial shocking terminal ($A_L$ COIL) 48, and a left ventricular shocking terminal ($V_L$ COIL) 49 which are adapted for connection to the left ventricular ring electrode 26, the left atrial tip electrode 27, the left atrial coil electrode 28, and the left ventricular coil electrode 29, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (N/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also be able to support high output pacing in accordance with the present invention. The high output pacing pulses may have energies of about 0.1 millijoules or greater. To support such pacing and other energy requirements of the device, the battery 110 may be a carbon monofluoride battery, known in the art as a $CF_X$ battery.

As further shown in FIG. 2, the device 10 has an impedance measuring circuit 1112 which is enabled by the microcontroller 60 via a control signal 114. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Now that the device 10 has been more generally described, the following description will be directed to those elements and features more directly related to this embodiment of the present invention.

The device 10, in accordance with the present invention is capable of providing high output far-field pacing for treating patients having severe infarcts and conduction abnormalities. Such patient may be CHF patients, for example.

The conduction abnormalities may be manifested in any number of different abnormal hemodynamic parameters such as cardiac output or QRS width. For example, wider or longer QRS widths indicate such abnormalities. When the QRS width reaches a certain duration, such as, for example 150 milliseconds, normal pacing of the ventricles including biventricular pacing at normal pacing energies will not shorten the QRS width to a normal width. However, high output far-field pacing will reduce the QRS width back to normal for such patients. The pacing energies preferably are about 0.1 millijoules or greater.

Still, normal near-field pacing should be maintained as long as the QRS width is below a certain limit. As will be seen hereinafter, in accordance with this embodiment, normal bipolar ventricular pacing is maintained as long as the QRS width is less a first predetermined duration of, for example, 150 milliseconds. Then, the device switches from normal near-field bipolar pacing to high output far-field pacing which is begun at a maximum output of, for example, 30 volts and gradually decreased when the QRS width shortens. When the QRS width reduces to a second predetermined duration, of for example 100 milliseconds, the device reverts back to normal pacing. The far-field pacing preferably utilizes large area electrodes such as defibrillation coil electrodes. In accordance with this embodiment, the far-field pacing electrodes may be the right ventricular coil electrode 36 and the left ventricular coil electrode 29. For normal pacing, the device may utilize the bipolar pacing electrodes 32 and 34.

As will be noted in FIG. 2, the microcontroller includes a QRS width measuring stage 62. The stage 62 measures the QRS width to control the far-field pacing energies and the switching between the near-field pacing electrode configuration of electrodes 32 and 34 and the far-field pacing electrode configuration of defibrillation electrodes 36 and 29.

Figure 3:
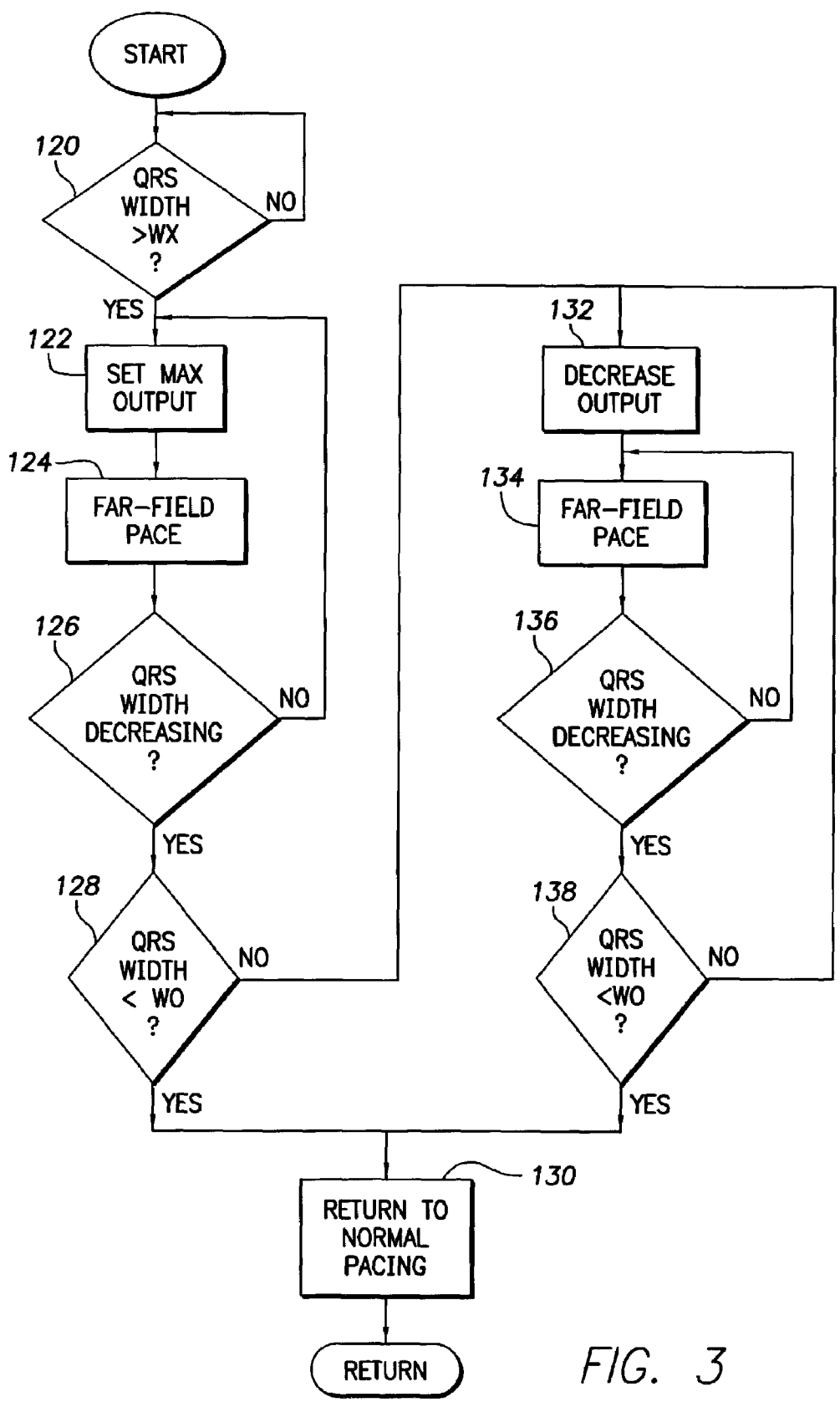
FIG. 3 is a flow chart describing an overview of the operation of one embodiment of the present invention.

In FIG. 3, a flow chart is shown describing an overview of the operation and novel features implemented in one embodiment of the device 10. In this flow chart, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

The following description of the flow chart of FIG. 3 assumes that the device is in a normal pacing mode using bipolar electrodes 32 and 34. It also assumes that the normal pacing mode provides pacing pulses with energies in the traditional pacing energy ranges and that after each cardiac cycle, the QRS width measuring stage 62 measures the most recent QRS width.

The process of FIG. 3 initiates at a decision block 120 wherein it is determined if the most recently determined QRS width is greater than a first predetermined duration ($W_x$) of, for example, 150 milliseconds. If the QRS width is not greater than the first predetermined duration, the process returns. However, if the most recently measured QRS width is greater than the first predetermined duration, the process then immediately advances to activity block 122 wherein the device sets the ventricular pulse generator 72 to its maximum output of, for example, 30 volts. After the output of the ventricular pulse generator 72 is set to its maximum output, the process then advances to activity block 124 wherein the switch 74 couples the ventricular pulse generator 72 to the far-field pacing electrode configuration. As previously mentioned, the far-field pacing electrode configuration may include the defibrillation coil electrodes 29 and 36. Activity block 124 further contemplates that once switch 74 couples the ventricular pulse generator 72 to the far-field pacing electrode configuration, the pulse generator 72 applies the high output far-field pacing pulse between electrodes 29 and 36.

Following activity block 124, the process then advances to decision block 126 wherein it is determined if the QRS width resulting from the far-field pacing pulse is decreasing. If the QRS width is not decreasing, the process returns to activity block 122 wherein the maximum output of the ventricular pulse generator 72 is once again set. However, if the QRS width is decreasing, the process then advances to decision block 128 wherein it is determined if the QRS width has been reduced to below the second predetermined duration of, for example, 100 milliseconds. If the QRS width has been reduced to below the second predetermined duration, the process then advances to activity block 130 wherein the device returns to normal pacing. Following activity block 130 the process returns.

If, in decision block 128, it is determined that the QRS width is still above the second predetermined duration, but is decreasing, the process then advances to activity block 132. Here, the output of the ventricular pulse generator is incrementally decreased. The incremental decrease may be, for example, 5 volts. Once the output has been decreased incrementally in accordance with activity block 132, the process then advances to activity block 134 wherein the ventricular pulse generator 72 applies a far-field pacing pulse to electrodes 29 and 36. Following the far-field pacing pulse applied in activity block 134, the process then advances to decision block 136 wherein it is determined if the QRS width is now decreasing. If the QRS width is not now decreasing, the process returns to activity block 134 for repeating the far-field pacing pulse at the incrementally reduced output. If the QRS width is decreasing, the process then advances to decision block 138 wherein it is determined if the QRS width has been reduced to below the second predetermined duration. If it has not, the process then returns to activity block 132 wherein the far-field pacing pulse energy is incrementally decreased again. This is then followed by the application of a far-field pacing pulse at the second incrementally decreased pacing pulse energy.

However, if in decision block 138 it is determined that the QRS width has been reduced to below the second predetermined duration, the process then advances to activity block 130 wherein normal pacing is resumed. The process then returns.

As can be seen from the foregoing, in the embodiment of FIG. 3, if the QRS width is decreasing but has not yet been reduced to below the second predetermined duration, the far-field high output pacing pulse energy is incrementally reduced. This process continues until the QRS width has been reduced to below the second predetermined duration of, for example, 100 milliseconds, wherein normal pacing is once again resumed.

While the invention has been described by means of specific embodiments and applications thereof, it is understood that numerous modifications and variations may be made thereto by those skilled in the art without departing from the spirit and scope of the invention. It is therefore to be understood that within the scope of the claims, the invention may be practiced otherwise than as specifically described herein.

What is claimed is:

1. An implantable cardiac stimulation device comprising:
   a pulse generator that provides pacing pulses having energies greater than about 0.1 millijoules;
   a lead system comprising a far-field electrode configuration comprising at least one electrode in a first chamber and at least one electrode in a second chamber, wherein the far-field electrode configuration is operative to apply the pacing pulses between the first and second chambers; and a hemodynamic measuring circuit that measures a hemodynamic parameter of the heart and wherein the pulse generator varies the pacing energies to effect the hemodynamic parameter.

2. The device of claim 1 wherein the far-field electrode configuration comprises a right ventricular electrode and a left ventricular electrode.

3. The device of claim 2 wherein the electrodes are defibrillation electrodes.

4. The device of claim 2 wherein the electrodes are coil electrodes.

5. The device of claim 1 wherein the hemodynamic parameter is QRS width.

6. The device of claim 1 wherein the pulse generator varies the pacing energies responsive to the measured hemodynamic parameter.

7. The device of claim 1 wherein the lead system further comprises a near-field pacing electrode configuration.

8. The device of claim 7 further comprising a switch that selectively couples the pulse generator to the far-field and near-field electrode configurations.

9. The device of claim 8 wherein the switch selectively couples the pulse generator to the far-field and near-field electrode configurations responsive to the measured hemodynamic parameter.

10. An implantable cardiac stimulation device comprising:
    stimulation means for providing pacing pulses having energies greater than about 0.1 millijoules:
    means for applying the pacing pulses between first and second chambers of a heart, and
    hemodynamic parameter measuring means for measuring a hemodynamic parameter of the heart and wherein the stimulation means comprises means for varying the pacing energies to effect the hemodynamic parameter.

11. The device of claim 10 wherein the means for applying comprises a right ventricular electrode and a left ventricular electrode.

12. The device of claim 11 wherein the electrodes are defibrillation electrodes.

13. The device of claim 11 wherein the electrodes are coil electrodes.

14. The device of claim 10 wherein the hemodynamic parameter is QRS width.

15. The device of claim 10 wherein the stimulation means varies the pacing energies responsive to the measured hemodynamic parameter.

16. The device of claim 10 wherein the lead means further comprises a near-field pacing electrode configuration.

17. The device of claim 16 further comprising switch means for selectively coupling the stimulation means to the f-ar-field and near-field electrode configurations.

18. The device of claim 17 wherein the switch means selectively couples the stimulation means to the far-field and near-field electrode configurations responsive to the measured hemodynamic parameter.

19. A method of pacing a heart, the method comprising:
    providing pacing pulses having energies greater than about 0.1 millijoules;
    applying the pacing pulses to the heart with a far-field electrode configuration; and
    measuring a hemodynamic parameter of the heart and varying the pacing energies to effect the hemodynamic parameter.

20. The method of claim 19 wherein applying the pacing pulses comprises applying the pacing pulses between a right ventricular electrode and a left ventricular electrode.

21. The method of claim 19 wherein varying the pacing energies comprises varying the pacing energies responsive to the measured hemodynamic parameter.

22. A method of treating congestive heart failure of a heart with an implantable cardiac stimulation device, the method comprising;
    generating pacing pulses with the implantable cardiac stimulation device;
    applying the pacing pulses between a right ventricle and a left ventricle; and
    measuring a hemodynamic parameter of the heart and varying pacing pulse energy responsive to the measured hemodynamic parameter.

23. The method of claim 22 wherein providing pacing pulses comprises providing pacing pulses that have energies of at least about 0.1 millijoules.

24. The method of claim 22 wherein measuring a hemodynamic parameter of the heart and varying pacing pulse energy responsive to the measured hemodynamic parameter comprises measuring a QRS width and varying pacing pulse energy when the QRS width is greater than a first predetermined duration.

25. An implantable cardiac stimulation device comprising:
    a pulse generator that is operative to generate pacing pulses; and
    a lead system comprising at least one electrode overlying a left ventricle and at least one electrode in a right ventricle;
    circuitry that is operative to apply the pacing pulses between the at least one electrode in the right ventricle and the at least one electrode overlying the left ventricle; and
    a hemodynamic measuring circuit that measures a hemodynamic parameter of the heart and wherein the pulse generator varies the pacing energies to effect the hemodynamic parameter.

26. The device of claim 25 wherein the electrodes are defibrillation electrodes.

27. The device of claim 25 wherein the electrodes are coil electrodes.

28. The device of claim 25 wherein the hemodynamic parameter is QRS width.

29. A method of treating congestive heart failure, the method comprising:
    measuring a hemodynamic parameter of a heart;
    determining whether the measured hemodynamic parameter is indicative of heart failure;
    generating pacing pulses with the implantable cardiac stimulation device; and
    applying the pacing pulses between a right ventricle and a left ventricle if the measured hemodynamic parameter is indicative of heart failure.

30. The method of claim 29 wherein providing pacing pulses comprises providing pacing pulses that have energies of at least about 0.1 millijoules.

31. The method of claim 29 further comprising varying pacing pulse energy responsive to the measured hemodynamic parameter.

32. The method of claim 29 wherein measuring a hemodynamic parameter comprises measuring a QRS width.

* * * * *